US011083842B2

(12) United States Patent
Chassot

(10) Patent No.: US 11,083,842 B2
(45) Date of Patent: Aug. 10, 2021

(54) METHOD OF OPERATING AN INJECTION SYSTEM

(71) Applicant: ACIST MEDICAL SYSTEMS, INC., Eden Prairie, MN (US)

(72) Inventor: Pierre Yves Chassot, Thoiry (FR)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 593 days.

(21) Appl. No.: 16/076,584

(22) PCT Filed: Feb. 8, 2017

(86) PCT No.: PCT/EP2017/052716
§ 371 (c)(1),
(2) Date: Aug. 8, 2018

(87) PCT Pub. No.: WO2017/137421
PCT Pub. Date: Aug. 17, 2017

(65) Prior Publication Data
US 2021/0187193 A1 Jun. 24, 2021

(30) Foreign Application Priority Data
Feb. 9, 2016 (EP) ..................................... 16154762

(51) Int. Cl.
A61M 5/168 (2006.01)
A61M 39/28 (2006.01)
(Continued)

(52) U.S. Cl.
CPC ...... A61M 5/16813 (2013.01); A61M 5/1407 (2013.01); A61M 39/28 (2013.01);
(Continued)

(58) Field of Classification Search
CPC ............ A61M 5/16813; A61M 5/1407; A61M 39/28; A61M 5/007
See application file for complete search history.

(56) References Cited

U.S. PATENT DOCUMENTS 3,800,794 A 4/1974 Georgi
4,105,028 A 8/1978 Sadlier et al.
(Continued)

FOREIGN PATENT DOCUMENTS

WO 2011119425 A2 9/2011
WO 2013078179 A1 5/2013
WO 2016010778 A1 1/2016

OTHER PUBLICATIONS

PCT Search Report and Written Opinion for PCT/EP2017/052716, dated Mar. 9, 2017.

Primary Examiner — Bradley J Osinski
(74) Attorney, Agent, or Firm — Vivicar Law, PLLC

(57) ABSTRACT

A solution is proposed for operating an injection system comprising a pressurizing unit and at least one supply station for supplying a medical fluid to the pressurizing unit, the supply station comprising at least one receptacle for containing said medical fluid, a delivery arrangement in fluid communication with the receptacle and the pressurizing unit for delivering the medical fluid to a patient, and clamping means associated with the delivery arrangement for regulating the flow of the medical fluid through the delivery arrangement. The method comprises the steps of: operating the pressurizing unit till a first injection procedure is completed; maintaining the injection system in a standby condition before a second injection procedure is started, and operating the pressurizing unit till the second injection procedure is completed. The step of maintaining the injec-
(Continued)

tion system in a standby condition comprises the step of acting on the clamping means for de-clamping the delivery arrangement.

17 Claims, 6 Drawing Sheets

(51) Int. Cl.
    *A61M 5/14*          (2006.01)
    *A61M 5/00*          (2006.01)
    *A61M 5/142*        (2006.01)

(52) U.S. Cl.
    CPC ......... *A61M 5/007* (2013.01); *A61M 5/14228* (2013.01); *A61M 2205/502* (2013.01)

(56) References Cited

U.S. PATENT DOCUMENTS

| | | | |
|---|---|---|---|
| 4,512,764 A | | 4/1985 | Wunsch |
| 4,559,036 A | * | 12/1985 | Wunsch ............ A61M 5/16827 |
| | | | 604/81 |
| 2012/0232383 A1 | | 9/2012 | Duffour et al. |
| 2013/0138074 A1 | | 5/2013 | Travis et al. |

* cited by examiner

METHOD OF OPERATING AN INJECTION SYSTEM

CROSS-REFERENCE TO RELATED APPLICATIONS

This application is the national stage application of corresponding international application number PCTEP2017/052716, filed Feb. 8, 2017, which claims priority to and the benefit of European application no. 16154762.5, filed Feb. 9, 2016, all of which are hereby incorporated by reference in their entirety.

TECHNICAL FIELD

The present disclosure relates to the field of medical equipment. More specifically, the present disclosure relates to injection systems.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

The injection of fluids into patients is commonplace in several medical procedures. For example, a contrast agent (or contrast medium) may be injected, possibly along with a saline solution, to enhance contrast of target (body) features (for example, human body's structures or organs) within the patients during scan examinations thereof. Particularly, in imaging applications (wherein a visual representation of the interior of the patients is created in a non-invasive way without turning to surgery techniques) the use of a contrast agent makes the target features more conspicuous. As a result, target features that would otherwise be less distinguishable from other nearby features (for example, surrounding tissues) are highlighted. This significantly facilitates the task of clinicians in diagnostic applications, and particularly the identification and/or characterization of lesions, the monitoring of their evolution or the response to medical treatments. For example, a iodine-based contrast agent (such as comprising iopamidol) is commonly used in Computed Tomography (CT) applications (such as angiography investigations).

The contrast agent is usually injected into a blood vessel of a patient by an (automated) injection system. The injection system pressurizes the contrast agent and injects it into the patient under predetermined injection conditions, for example, at a predetermined flow rate and volume. In this way, the contrast agent may be injected in a controlled, safe and efficient manner.

Typically, the contrast agent is provided in (rigid) bottles. Therefore, the injection system is provided with one or more supply stations, each one for supplying the contrast agent to be injected from a corresponding bottle. For this purpose, the supply station comprises a bottle holder that holds the bottle (turned up-side-down) in position and connects it to a delivery arrangement for finally delivering the contrast agent to the patient. Typically, the supply station also comprises a protective cover, which is mounted on the bottle holder so as to protect the bottle held thereon from external accidental shocks.

The bottle holder and the protective cover define a (closed) chamber, which may also provide for a thermal insulation of the bottle. This facilitates maintaining a target temperature of the contrast agent to be injected during the scan examination. Indeed, the contrast agent generally has a relatively high viscosity. The viscosity of the contrast agent may adversely affect its correct injection in the patient (for example, since occurring at a flow rate lower than it is desired). In any case, this requires the application of a relatively high pressure (with an increase in complexity, and then cost, of the injection system). Moreover, the injection of the contrast agent with high viscosity and at high pressure is quite uncomfortable for the patient. However, the viscosity of most contrast agents may be reduced by increasing their temperature. Therefore, the contrast agent is generally pre-warmed before being injected by using a dedicated equipment (for example, a warmer) separated from the injection system. For example, contrast agents pre-warmed to a target temperature close to the body temperature (such as 35-37° C.) may halve their viscosity. In this way, it is easier to inject the contrast agent efficiently (for example, at the desired flow rate) with lower pressure (and then lower complexity and cost of the injection system) and higher comfort for the patient. Moreover, in order to mitigate the cooling of the contrast agent due to the inevitable heat loss, some injection systems comprise a heating device that is controlled to warm the contrast agent to be injected, so as to maintain it at the target temperature (i.e., close to the body temperature) during the whole scan examination procedure.

As mentioned above, an injection system typically comprises a delivery arrangement that is positioned in fluid communication with at least one supply station and a pressurizing unit for injecting a patient with a medical fluid (e.g. a contrast agent, a saline solution or a mixture thereof). Since the delivery arrangement is positioned upstream of the pressurizing unit and, therefore, it is not in direct connection with a patient, with substantially no risk or a very low risk of cross-contamination, generally the delivery arrangement is a disposable element that is changed periodically (for example, every 10 or 12 hours). This means that the delivery arrangement is not changed when a new patient is submitted to examination and it is typically kept in place for multiple successive injections, till the predetermined period of time designed for the delivery arrangement is fully elapsed.

In order to reduce the overall costs associated with managing and operating an injection system, especially in order to avoid discarding injector components that are underexploited due to a limited use of the injection system (e.g. only one or very few injection procedures have been carried out after the installation of a new delivery arrangement), the Applicant has perceived the need of providing a delivery arrangement that can be used for a longer time with respect to the known and traditional delivery arrangements, without undermining the safety of the overall injection system, e.g. in terms of cross-contamination risks among successive patients being examined with the same injector.

Moreover, providing a delivery arrangement that can ensure an increased usage time clearly represents an advantage also in terms of efficiency of the medical unit (e.g. hospital or clinic) where the injection system is installed. In fact, it's not unusual that a patient is admitted to the hospital emergency room and he requires an urgent examination, such as a CT scan for which an injection system is used. It is apparent that the injection system present in an emergency room is reserved to emergencies only, and thus it is not planned to be used for programmed patients of the hospital daily activity. Therefore, it may happen that the injection system of the emergency room is ready to inject (with the delivery arrangement being installed) because a patient was previous treated, but the successive patient is admitted when the usage time of the delivery arrangement has already elapsed. This means that in an emergency situation the operator has to replace the used delivery arrangement with a new one, thereby spending very important time to install it and prime the injector, putting at risk the patient's health and life.

The Applicant has thus designed and manufactured a delivery arrangement which can advantageously be substituted every 24 hours, thereby remarkably increasing (even doubling) the usage time of such a disposable element.

However the Applicant has noticed that, by increasing to such an extent the usage time of the delivery arrangement, some undesired technical drawbacks can occur in case the injection system is used only few times during the allowed (and designed) usage time of the delivery arrangement.

In fact, as better explained in the following of the present description, in order to properly inject the medical fluid contained in a given receptacle of a supply station of an automated, syringe-less injector, a clamping means is associated to the delivery arrangement which is in fluid communication with both the pressurizing unit and the receptacle. In fact, in cooperation with the pressurizing unit, by properly acting on the clamping means a desired amount of the medical fluid, at a desired flow rate, is caused to flow through the delivery arrangement. In detail, the clamping means acts on the external surface of the delivery arrangement tubing that exits from the receptacle and then enters the pressurizing unit, the delivery arrangement tubing being connected to a separate patient delivery set tubing for injecting the medical fluid into a patient. When an injection procedure is started and the medical fluid is poured out from the receptacle, the respective clamping means is in a de-clamping state, thereby allowing the medical fluid to flow through the tubing of the delivery arrangement. On the contrary, when an injection procedure is not performed or a second medical fluid is caused to be poured out from a second receptacle during an injection procedure, the clamping means associated to the delivery arrangement tubing exiting from the first receptacle is in a clamping state and the tubing flow passage section is reduced so that flowing of the medical fluid (through the delivery arrangement tubing) is prevented.

Therefore, increasing the usage time of the delivery arrangement implies that also the period of time during which the clamping means is in a clamping state (and thus it clamps the installed delivery arrangement to stop the medical fluid flow) can potentially increase if, after a first injection procedure, the injection system is no longer operated or if it is operated only few times with long pause times between two successive injection procedures. In fact the Applicant noticed that, if the delivery arrangement tubing remains clamped for a long time, sometimes it may happen that de-clamping does is not properly executed or it is partially executed by the injection system. This is due to the fact that, if the tubing remains squeezed for a long period of time, the opposite surfaces of the tubing wall (that are pressed the one against the other for closing the tubing inner passage and preventing the medical fluid to flow there into), stick to each other and the tubing is not able to recover its original cylindrical shape. This event is clearly undesirable since the correct functioning of the injection system cannot be guaranteed if the clamping means are not properly operated. It is apparent that, if the clamping means is requested to be activated in the de-clamping function at a predetermined step of the injection procedure and this action is not performed (because the tubing wall remains completely squeezed and stuck and the regular flow of the medical fluid is substantially prevented) or it is only partially performed (because the tubing wall is partially stuck and the regular flow of the medical fluid is partially prevented) or it is performed with a certain delay (because the tubing requires more time to fully recover its original shape), the flowing of the medical fluid does not occur or it occurs only partially, and the desired correct injection procedure is not provided to the patient.

Since the increase of the usage time of the delivery arrangement is clearly considered as an advantageous solution both from economic and patient's safety perspectives as indicated above, the Applicant has perceived the need of finding a technical solution which can overcome the stickiness problems that may nullify the benefits of the new, long duration delivery arrangement.

U.S. Pat. No. 3,800,794 discloses a method and an apparatus for parenteral administration of medical fluids, wherein a normally shut-off intravenous feeding tube is selectively opened at a given frequency and the open period duration is automatically regulated by a digital control system to establish a fluid flow rate at any selected rate over a wide dynamic range. Measured and desired flow rates are converted to digital electrical signals and compared, the electrical difference being used to vary a control voltage which establishes the width of energizing pulses controlling a member for opening the feeding tube.

U.S. Pat. No. 4,105,028 discloses a method and an apparatus for parenteral administration of medical fluids comprising a normally closed clamp on the intravenous feeding tube which is opened by means of an electromagnetic actuator at a preselected drop frequency rate and closed when a drop is detected by a conductive path established by the drop passing between two opposing electrodes. The electrical system governing the drop counting electrodes also is provided with drop size measuring means which acts to control the preselected drop frequency rate wherein a desired volumetric rate is maintained.

Document US 2012/0232383—in the name of the same Applicant—discloses a medical device for injecting contrast media including at least two separate vessels and immiscible contents inside one and/or both of the vessels, an injector and a distributor arranged such as to establish alternating communication between said vessels and said injector, said medical device being characterized in that it includes a means for providing said alternating communication at a frequency of 0.2 to 5 Hz.

It can be noted that the above prior art documents disclose clamping and de-clamping sequences that are carried out as part of an injection procedure, i.e. as steps that are performed for injecting proper rates and/or amounts of one or more medical fluid during injection thereof.

U.S. Pat. No. 4,512,764 discloses a manifold for sequentially dispensing a plurality of solutions through an intravenous supply catheter. The manifold includes a disposable tubing manifold that is connected to each of the solutions to be administered. Flow of solution through the branches of the tubing manifold can be stopped by valves which engage each branch. The quantity of solution dispensed is metered by a volumetric infusion pump and controlled by sequentially opening and closing the valves individually.

SUMMARY

A simplified summary of the present disclosure is herein presented in order to provide a basic understanding thereof;

however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure relates to a method of operating an injection system so that, when the latter is in a standby condition (i.e. it is not operated), stickiness of the delivery arrangement is substantially prevented.

Particularly, an aspect of the present disclosure provides a method of operating an injection system which comprises the step of acting on the clamping means associated to the delivery arrangement so that de-clamping thereof is activated at a predetermined de-clamping frequency when the injection system is in a standby condition.

In other words, the Applicant has found that stickiness of the clamped tubing of the delivery arrangement can be avoided and substantially prevented if de-clamping of the clamping means acting on the delivery arrangement is performed at regular time intervals when the injection system is in a standby condition occurring between two successive injection procedures.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
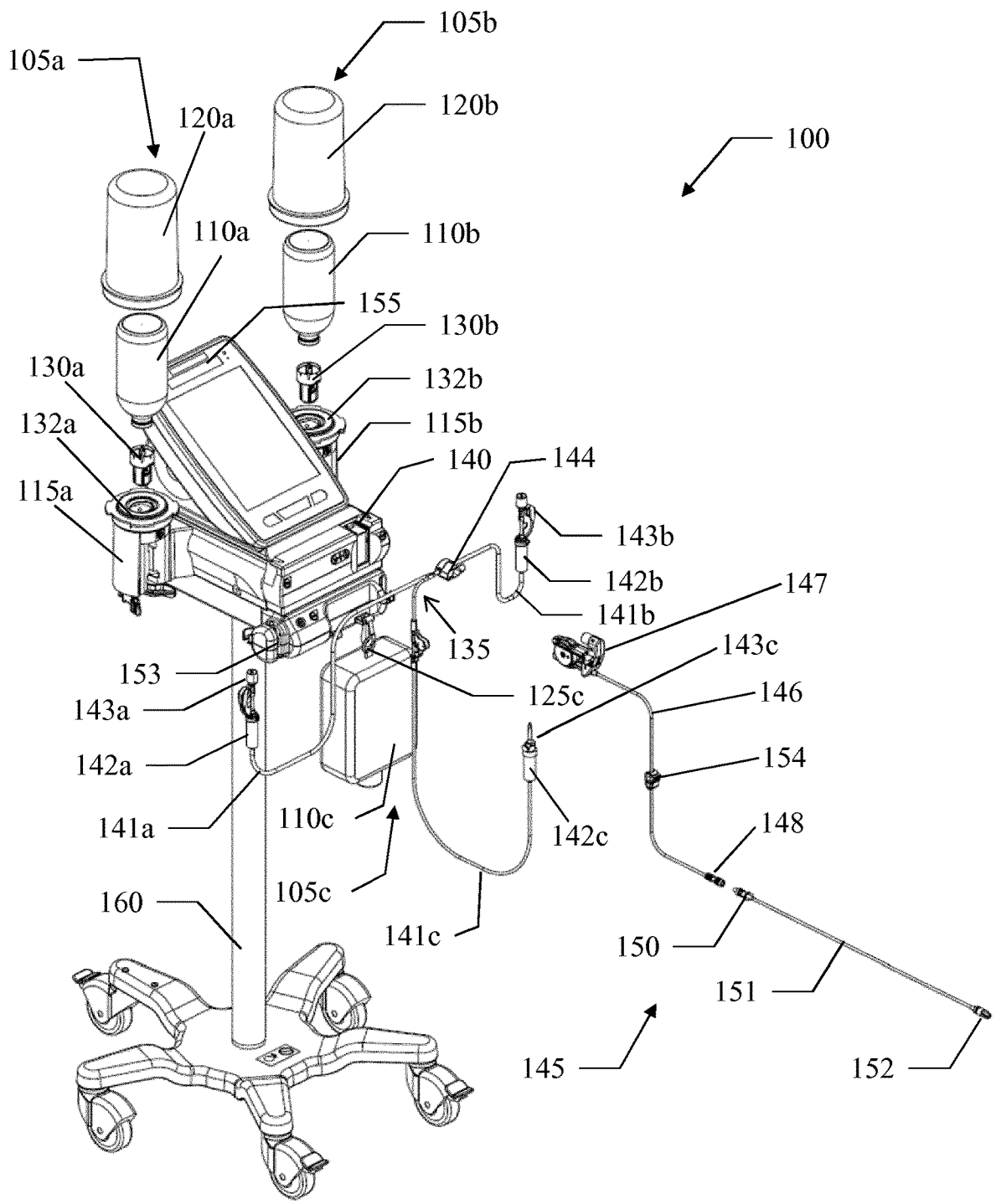
FIG. 1 shows a pictorial representation in partially exploded perspective view of an injection system wherein the solution according to an embodiment of the present disclosure may be applied.

With reference in particular to FIG. 1, a pictorial representation in partially exploded perspective view is shown of an injection system 100 wherein the solution according to an embodiment of the present disclosure may be applied.

The injection system 100 is used to inject one or more medical fluids into a patient (not shown in the figure). Particularly, the injection system 100 is an automated syringe-less injector that is used by clinicians to inject contrast agent and saline solution during scan examinations (for example, in radiography applications like CT scans).

The injection system 100 shown in FIG. 1 comprises a first supply station 105a, a second supply station 105b and a third supply station 105c for supplying the medical fluids to be injected from corresponding receptacles. Particularly, the supply station 105a and the supply station 105b supply a medical fluid from a bottle 110a and from a bottle 110b, respectively (i.e., a container made from glass or rigid plastic). On the contrary, the supply station 105c supplies a medical fluid from a pouch 110c (i.e., a container made from soft plastic). The supply stations 105a, 105b may be used to supply one or more contrast agents (to enhance contrast of specific body features within the patient), or a contrast agent and a saline solution (comprising a physiological or isotonic solution) respectively, whereas the supply station 105c may typically be used to supply the saline solution. For example, in CT applications the contrast agent may be a iodine-based contrast agent comprising diatrizoate, ioxaglate, iopamidol, iohexol, ioxilan, iopromide or iodixanol, and the saline solution may be sodium chloride. An example of a commercial contrast agent comprising iopamidol is ISOVUE, manufactured by Bracco Diagnostics Inc. (trademarks). Each bottle 110a, 110b may contain a single or multiple dose (for example, 50-500 ml) of different contrast agents (a first contrast agent in the first bottle and a second different contrast agent in the second bottle, the two contrast agents to be supplied in a predetermined sequence) or of the same contrast agent (to be supplied in succession to increase the duration of the scan examination). The pouch 110c generally contains a bulk of saline (for example, 100-1,000 ml) to be supplied before (pre-flush), after (post-flush) or between (interphase) injections of the contrast agent, or alternatively in rapid alternate succession with the contrast agent (to achieve a mixing of the contrast agent and the saline solution within an organ of the patient, for example within the heart). Alternatively, as mentioned above, the supply stations 105a and 105b may be used to supply a contrast agent and a saline solution, respectively. In this latter case the supply station 105c can be eliminated.

More specifically, each supply station 105a, 105b (respectively) comprises a bottle holder 115a, 115b for housing and supporting the bottle 110a, 110b. A protective cover 120a, 120b may be mounted on the bottle holder 115a, 115b to cover the bottle 110a, 110b when it is held thereon, thereby defining a (closed) chamber for housing the bottle 110a, 110b. The bottle holder 115a, 115b and the protective cover 120a, 120b protect the bottle 110a, 110b from external accidental shocks. Moreover, they are made of a thermally insulating material (for example, polycarbonate) to reduce heat losses, thereby helping to maintain warm (for example, at about the body temperature) the medical fluid contained in the bottle 110a, 110b, which was previously heated in a dedicated device separate from the injection system (not shown). Typically the supply station 105c instead simply comprises a hook 125c for hanging the pouch 110c.

The injection system further comprises a delivery arrangement 135 which determines a fluid pathway for delivering the medical fluids from the receptacles 110a, 110b, 110c to a pressurizing unit 140.

For this purpose, in each supply station 105a, 105b a bottle connector 130a, 130b is arranged in a connection port 132a, 132b of the bottle holder 115a, 115b. The bottle connector 130a, 130b comprises a spike for connecting to the bottle 110a, 110b and a connection element (for example, a septum or a male luer lock fitting) in fluid connection with the spike. The spike and the connection element are located at opposite longitudinal ends of the bottle connector 130a, 130b. Typically, the bottle connector 130a, 130b also comprises a filtering unit (not shown in the figure) between its spike and connection element. The bottle connector 130a, 130b is a disposable element for use with a single bottle 110a, 110b (for example, with the spike that breaks off and remains inside the bottle 110a, 110b when the bottle connector 130a, 130b is removed in order to prevent any accidental re-use thereof).

The delivery arrangement 135 (which is often indicated by the technicians as "Day Set" or "Transfer Set") connects all the supply stations 105a, 105b, 105c to the pressurizing unit 140 for transferring the corresponding medical fluids from the receptacles 110a, 110b, 110c to the pressurizing unit 140. The delivery arrangement 135 comprises a transfer line for each supply station 105a, 105b, 105c. The transfer line of each supply station 105a, 105b comprises a flexible tubing 141a, 141b that is provided (at a distal end thereof with respect to the pressurizing unit 140) with a reservoir (or drip chamber) 142a, 142b and a connection element 143a, 143b for mating with the connection element of the bottle connector 130a, 130b. For example, the connection element 143a, 143b is a spike in case the connection element of the bottle connector 130a, 130b is a septum, or the connection element 143a, 143b is a female luer lock fitting in case the connection element of the bottle connector 130a, 130b is a male luer fitting. During operation of the injection system 100, the reservoir 142a, 142b and the connection element 143a, 143b are arranged inside the bottle holder 115a, 115b. The transfer line of the supply station 105c comprises a flexible tubing 141c that is provided (at a distal end thereof with respect to the pressurizing unit 140) with a reservoir (or drip chamber) 142c and a spike 143c for connecting to the pouch 110c. All the flexible tubings 141a, 141b, 141c are coupled (at their proximal ends with respect to the pressurizing unit 140) with a T-connector 144, which comprises a plug for insertion in a corresponding port of the pressurizing unit 140.

The pressurizing unit 140 comprises an electric motor (not visible in the figure) of a peristaltic pump, which is used to pressurize the medical fluids (received from the receptacles 110a, 110b, 110c via the delivery arrangement 135) for their injection into the patient (for example, up to a pressure of 8 bar, or at a flow rate from 0.5 to 9.9 ml/s).

The injection system 100 further comprises a patient set 145 that connects the pressurizing unit 140 to the patient for delivering the pressurized medical fluids thereto. The patient set 145 comprises a delivery line made of a flexible tube 146, which is provided (at a distal end thereof with respect to the patient) with a peristaltic pump 147. The latter is introduced into a dedicated port provided in the pressurizing unit 140 and it is also in fluid communication with the T-connector 144. The peristaltic pump 147 houses a rotor having a plurality of squeezing wheels, among which a corresponding portion of the flexible tube 146 is inserted. When the patient set 145 is of single use type (not shown in FIG. 1) for use by a single patient only, the flexible tube is quite long (remarkably longer than the flexible tube 146 shown in FIG. 1) and it is provided (at a proximal end thereof with respect to the patient) with a connection element for mating with a respective connection element (for example, a plug) of a peripheral catheter which is inserted through the skin into a peripheral vein of the patient to be treated. Instead, when the patient set 145 is of multiple use type (as shown in FIG. 1) for use by multiple patients, the flexible tube 146 (delivery line) is quite short and it is provided at the proximal end thereof with a connection element 148 for mating with a connection element 150 of an additional patient line (also indicated as patient line) made of a long flexible tube 151 (only partially shown in FIG. 1), which in turn ends with a connection element 152 for mating with the connection element of a peripheral catheter (not shown). The patient set 145 is a disposable element which, in case of single use, is for use entirely with a single patient, while, in case of multiple use, it is changed periodically (for example, every 12 hours), except for the additional patient line 150-152 which is for use with a single patient only and thus discarded and substituted with a new one when a new patient has to be treated. The flexible tube 146 can be also provided with a clip 154 that pinches the tube and closes the line during installation or uninstallation of the additional patient line 150-152.

Figure 3:
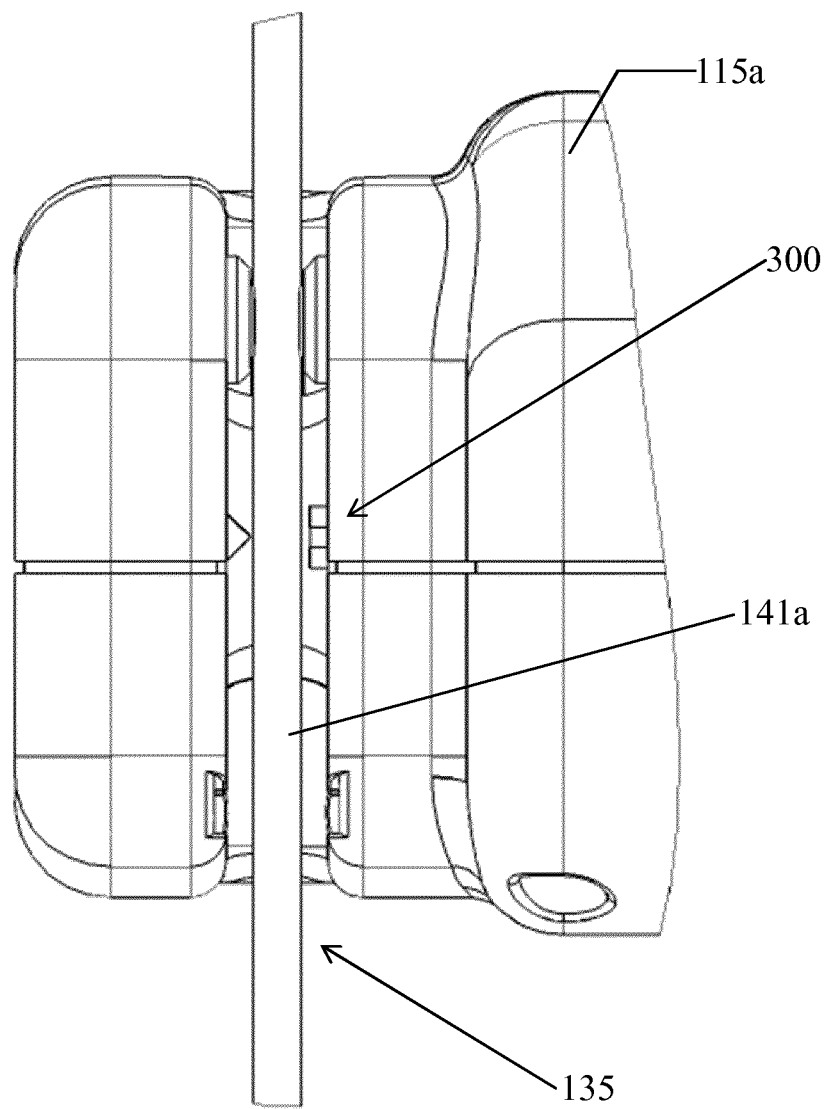
FIG. 3 shows a pictorial representation of the clamping means in its de-clamping state of the injection system shown in FIG. 1.
Figure 4:
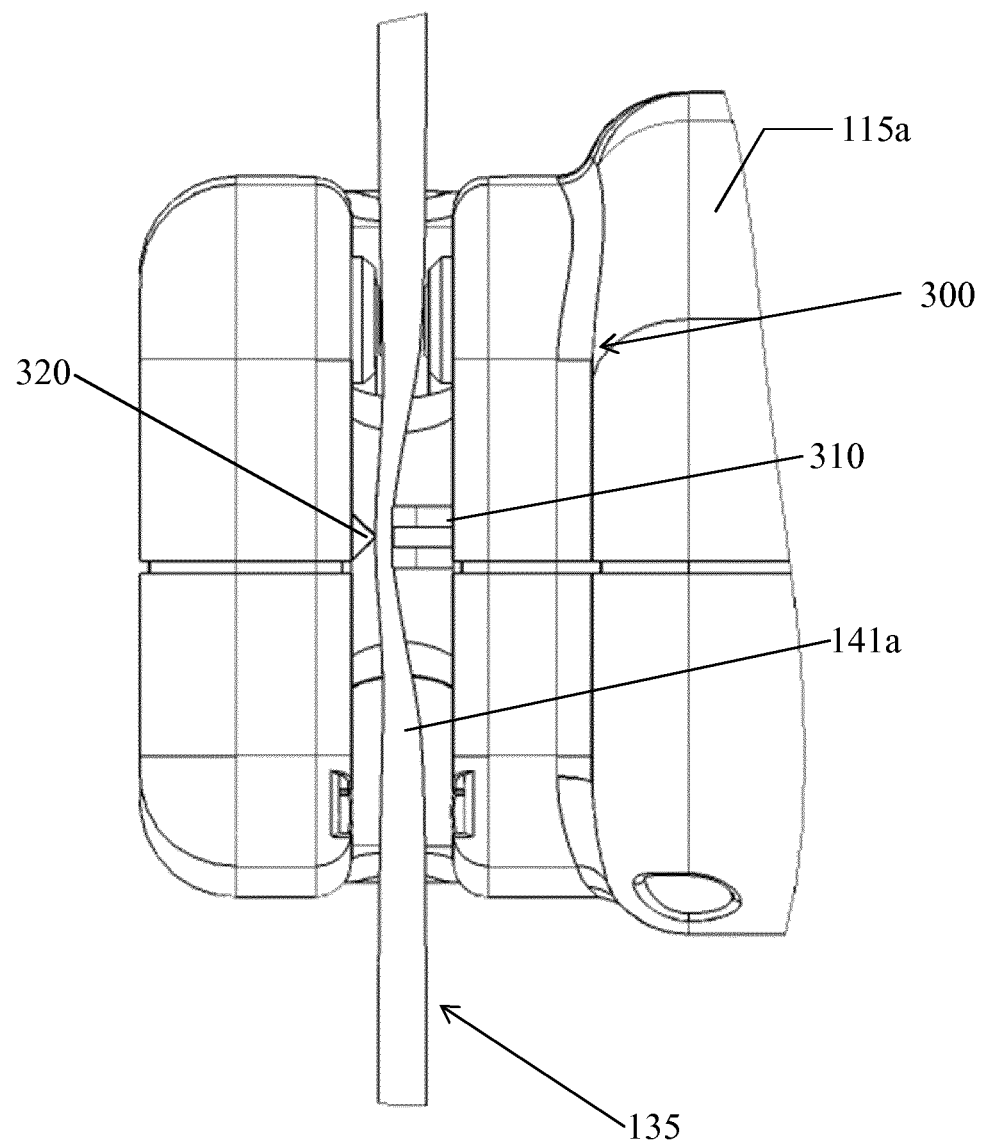
FIG. 4 shows a pictorial representation of the clamping means in its clamping state of the injection system shown in FIG. 1.

According to the embodiment shown in FIG. 1, each supply station 105a, 105b, 105c of the injection system 100 further comprises clamping means 300 (shown in detail in FIG. 3 and FIG. 4) for engaging the delivery arrangement 135 and thus blocking or unblocking the passage of the medical fluid flowing there into. Specifically, the clamping means 300 of supply station 105a, 105b is located inside the bottle holder 115a, 115b, while the clamping means 300 of supply station 105c is located in a dedicated seat 153 housed in the front part of the injector body. Clamping means 300 comprises a first component 310 that is operated in cooperation with a second component 320 that is laterally spaced apart from the first component 310. In fact the space which separates the two components from each other is suitable for receiving, respectively, the flexible tubing 141a, 141b, 141c of the delivery arrangement 135. The clamping means 300 is positioned perpendicularly to the flexible tubing 141a, 141b, 141c and the first component 310 is movable to urge against the second component 320 that, on the contrary, is in a fixed (static) position. According to the embodiment shown in FIG. 3 and FIG. 4, the first component 310 shifts along a direction that is substantially perpendicular to the longitudinal axis of the flexible tubing 141a, 141b, 141c so that the latter is suitably squeezed (between the first component 310 and the second component 320) to sensibly reduce its cross-sectional area and to prevent the flowing of the medical fluid there through. Optionally, the first component 310 is U-shaped while the second component 320 is wedge-shaped so that the interaction of the conical portion of the second component 320 with the open recess of the first component 310 causes the flexible tube to bend and to be restricted and squeezed. Therefore, the clamping means 300 is provided to act on the outer surface of the flexible tubing and to reduce its cross-sectional area in correspondence of the engagement region where first and second components 310, 320 interact. By way of clarification, reducing the cross-sectional area means that the tube wall portion which is engaged by the first component 310 comes into contact with the diametrically opposite tube wall portion that is engaged by the second component 320.

A control unit 155 controls the operation of the injection system 100. For example, the control unit 155 comprises a (main PCB) board with a microprocessor, a RAM that is used as a working memory by the microprocessor and a flash E²PROM that stores information to be preserved even when a power supply is off (particularly, a control program of the injection system 100). Moreover, the control unit 155 comprises a touch-screen and several buttons, which are used by an operator to interact with the control unit 155.

Activation (i.e. clamping and de-clamping) of the clamping means 300 is controlled automatically by the injector software, i.e. it is part of the injector program which also includes the priming step as well as the plurality of injection steps that can be carried out by the injector (according to the injection protocols that are loaded on the injector, typically on the injector remote console not shown in FIG. 1). The clamping means, in fact, as mentioned above, are already used during a normal operation of the injector. However, according to the present disclosure, the clamping means are also activated when the injector is in its standby condition to overcome the stickiness problems previously enunciated. Alternatively, activation of the clamping means 300 can be manually controlled by the operator by means of pressing a button present at each supply station.

The injection system 100 is supported by a stand 160. The stand 160 is provided with wheels to facilitate moving the injection system 100; moreover, the wheels have a foot brake to secure the injection system 100 in position.

Figure 2:
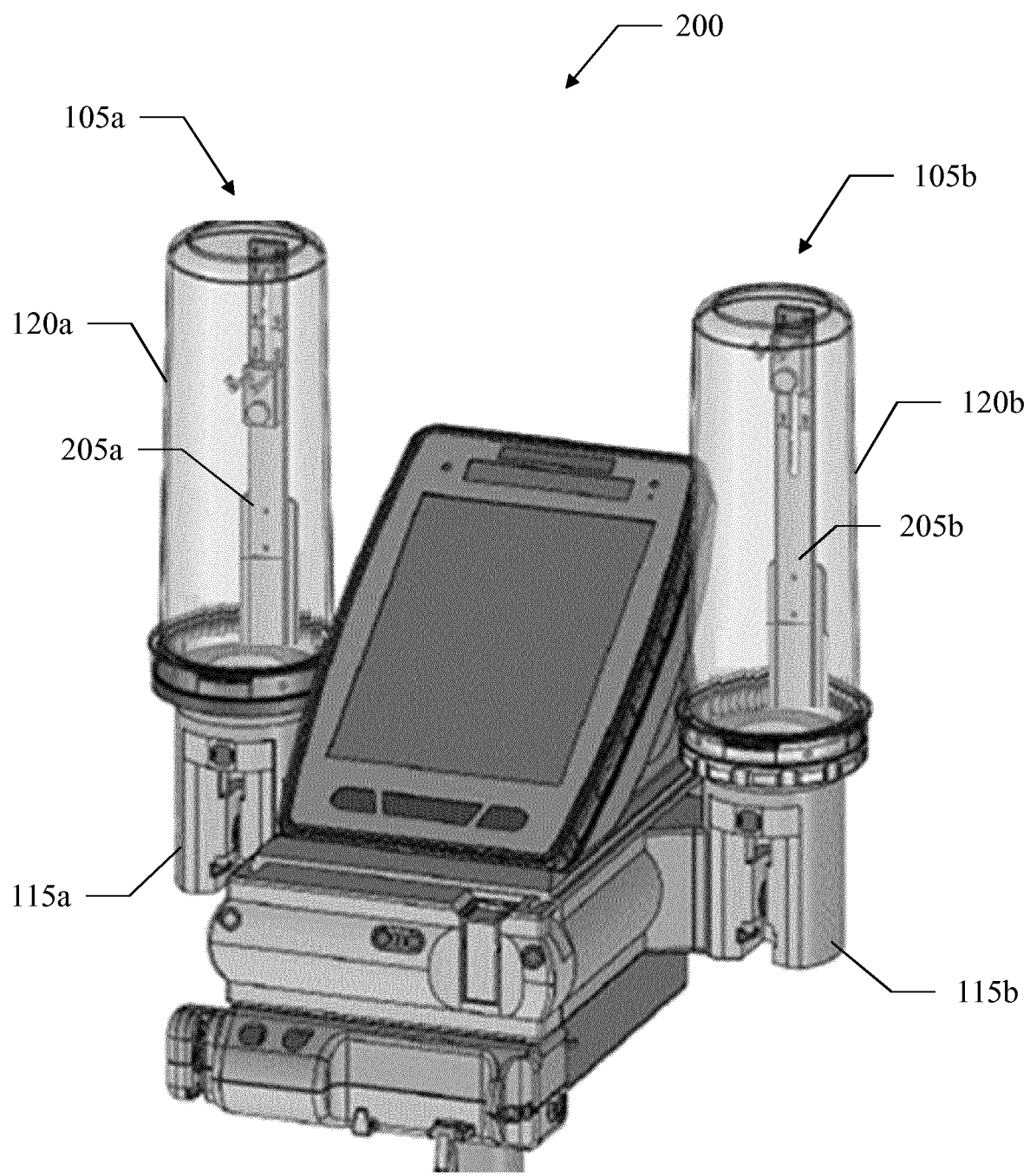
FIG. 2 shows a pictorial representation of a particular of an injection system according to an embodiment of the present disclosure.

With reference now to FIG. 2, a pictorial representation is shown of a particular of an injection system 200 according to an embodiment of the present disclosure.

The injection system 200 differs from the one described above (with respect to FIG. 1) for the addition of a bag (or pouch) holder 205a and a bag (or pouch) holder 205b in the supply station 105a and in the supply station 105b, respectively. Each bag holder 205a, 205b is used to hold a bag, not shown in the figure (i.e., a soft container not self-sustaining, for example, made of polypropylene). In this case as well, the bags of the two supply stations 105a, 105b may contain a single or multiple dose of different contrast agents or of the same contrast agent, or they may contain a contrast agent and a saline solution, respectively. Each bag holder 205a, 205b is configured for being mounted on the bottle holder 105a, 105b and then the protective cover 120a, 120b is mounted on the bag holder 205a, 205b.

The above-described solution makes the injection system 200 very versatile. Indeed, the injection system 200 may thus be used with contrast agents (or saline solutions) that are provided either in bottles (not shown in the figure), as in the most common cases, or in bags, so as to reduce the costs for their shipment/storage and to facilitate their disposal, or with any combination thereof. Moreover, this result is advantageously achieved without any (significant) structural change to the injection system 200; therefore, it is possible to retrofit standard (traditional) injection systems (designed for the bottles) in a very simple and cost effective way.

In operation, for each scan examination to be performed, the operator positions the injection system 100 close to the patient to be examined and then turns the injection system on. If it has not already been done, the operator installs the delivery arrangement 135 by inserting each reservoir 142a, 142b and connection element 143a, 143b into the corresponding bottle holder 115a, 115b (across a flap thereof) and releasably blocking them therein (for example, through a snap fitting mechanism). When the pouch 110c (containing the saline solution) is not installed, the control unit 155 displays a message on its screen prompting the operator to do so. If the pouch 110c is to be used, the operator pierces a seal of the pouch 110c with the spike 143c, hangs the pouch 110c from the hook 125c and fills the reservoir 142c completely with the saline solution (by repeatedly squeezing it). At this point, the operator programs the control unit 155 (either at the control unit 155 or at the injector remote console) by entering specific information relating to the saline solution of the pouch 110c (for example, its brand name and volume). Otherwise, if the pouch 110c is not used, the operator enters a corresponding command to the control unit 155 (or the remote console). In both cases, when the bottle 110a (with the contrast agent) is not installed, the control unit 155 displays a message on its screen prompting the operator to do so. In response thereto, the operator takes the bottle 110a from a separate warmer (not shown in the figures), wherein the bottle 110a has been pre-warmed to a target temperature; the target temperature is set to a value high enough to allow injecting the contrast agent efficiently (for example, at the desired flow rate) and comfortably for the patient, but not too high to be harmful for the patient (for example, 32-37.5° C.). The operator pierces a seal of the bottle 110a with the spike of the bottle connector 130a. The operator then turns up-side-down the bottle 110a (with the bottle connector 130a connected thereto), inserts the bottle connector 130a into the connection port 132a (so as to connect its connection element to the connection element 143a), mounts the protective cover 120a on the bottle holder 115a (so as to safely enclose the bottle 110a) and fills the reservoir 142a completely with the contrast agent (by repeatedly manually squeezing the reservoir 142a). At this point, the operator programs the control unit 155 (either at the control unit 155 or at the injector remote console) by entering specific information relating to the contrast agent of the bottle 110a (for example, its brand name and volume). The operator repeats the same operations, if it is necessary, to install the bottle 110b (with the contrast agent or with the saline solution). The control unit 155 now displays a message on its screen prompting the operator to install the patient set 145. In response thereto, the operator inserts the peristaltic pump 147 into the corresponding port of the pressurizing unit 140 and connects the peristaltic pump 147 to the T-connector 144. When the patient set 145 is for multiple use, the operator further connects the connection element 150 of the patient line 150-152 to the connection element 148 of the delivery line 146-148. The operator now separately primes each transfer line 141a-143a, 141b-143b and 141c-143c by selecting a corresponding priming function on the control unit 155 (or remote console), so as to eliminate any air bubbles that are possibly present within the transfer lines 141a-143a, 141b-143b and 141c-143c, the delivery line 146-148 and/or the (possible) patient line 150-152. Alternatively and preferably, the priming phase is advantageously automatically performed by the injection system without the need for the operator to execute it manually. Once this priming phase has been terminated (with no air that is sensed in the injection system 100 any longer), the operator finally connects the connection element 152 (or the connection element of the patient set in case of single use) to the connection element of the peripheral catheter (not shown) already introduced into the patient's blood vessel.

At this point, the operator programs the control unit 155 (or the remote console) by entering information relating to the scan examination (for example, the needle gauge of the peripheral catheter, the injection protocol comprising one or more injection phases each one defined by the type, volume and flow rate of the medical fluids, possibly selected among pre-defined injection protocols for different types of scan examinations).

The injection protocol (number of injection phases, sequence of injection phases, injection parameters like flow rate and duration time, contrast agent and saline details, needle gauge) specific for a given patient to be examined can be manually introduced by the operator through the control unit 155 (or the remote console). Alternatively, the operator can download the injection protocol from a removable memory, such as a USB flash drive. Alternatively, the operator can download the injection protocol, as well as the relevant patient's data, from a server which can connect more than one injection system 100 and, in case, also more than one clinical premises.

At this point of the injection procedure the operator can start the scan examination which combines the functionalities of the injection system with the functionalities of the imaging device, the latter being operated in conjunction with the injection system that provides the contrast agent activity which is used during the scan procedure. At the end of the scan examination, the operator turns the injection system 100 off, disconnects the delivery/patient line of the patient set 145 from the peripheral catheter, and then removes and discards it. Therefore, the injection procedure of the given examined patient can be considered completed.

As mentioned above, if the delivery arrangement 135 is a disposable element that can be changed every 24 hours (and not every 10 or 12 hours as it happens if a standard delivery arrangement is used), at the end of the injection procedure the delivery arrangement 135 is not discarded if its usage time has not elapsed yet, and it remains installed, ready for a new patient to be injected, i.e. a new injection procedure to be started.

The injection system 100 of FIG. 1 (as well as the injection system 200 of FIG. 2) comprises three separate supply stations 105a, 105, 105c. However, the present disclosure can be applied to an injection system that is provided with a single supply station. Analogously, the present disclosure can be applied to an injection system that is provided with two separate supply stations.

Figure 5:
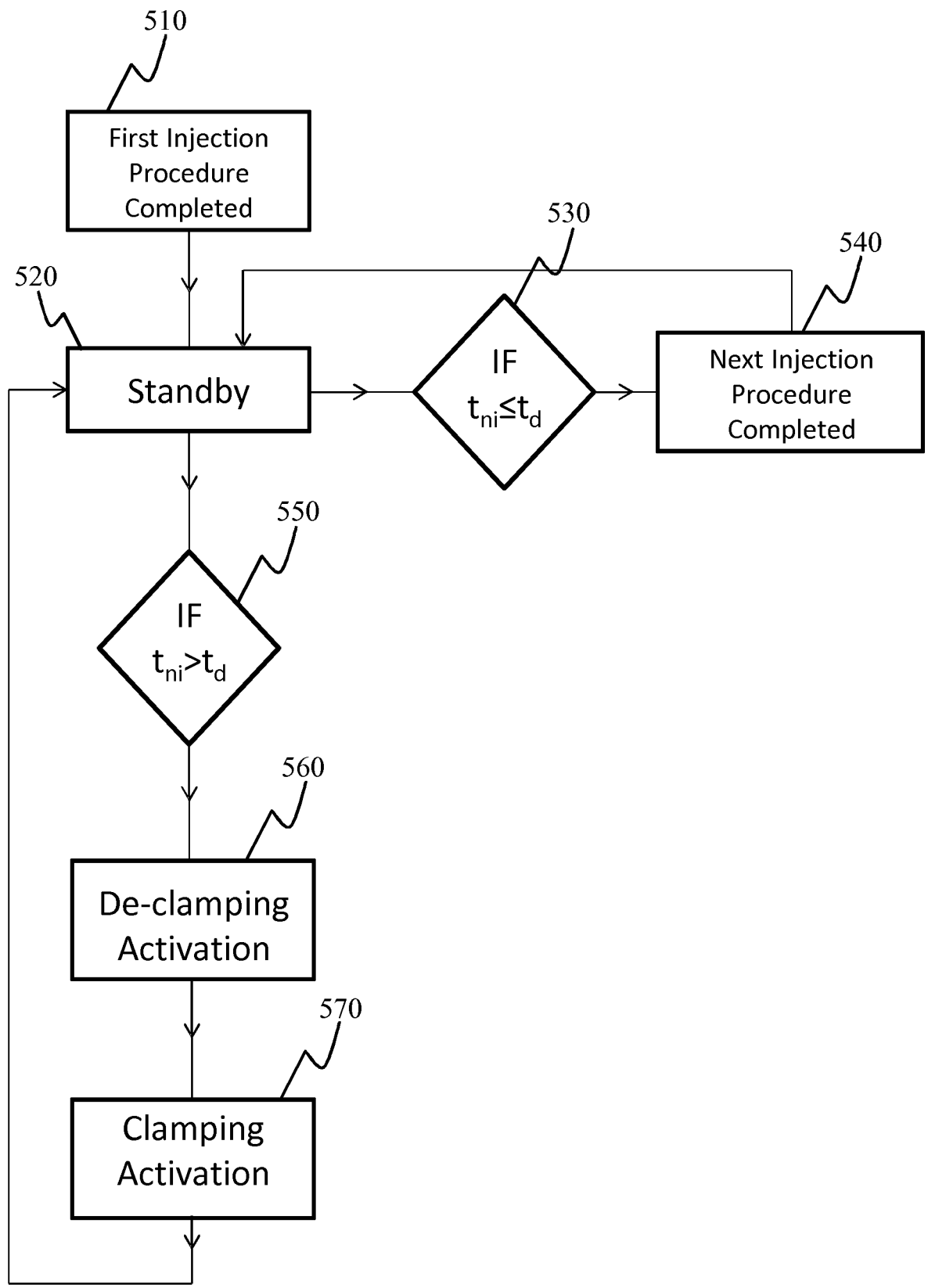
FIG. 5 shows a simplified flow chart of the method of the present disclosure.

Referring now to FIG. 5, a simplified flow chart is shown for better explaining the method of operating an injection system according to an embodiment of the present disclosure.

In detail, step 510 indicates that a first injection procedure on a first patient has been completed and the delivery arrangement 135 is not discarded being still within its 24 hours usage time.

As previously explained, it may happen that the injection system 100 is not operated to treat a second patient immediately after the injection on a first patient has been completed. This situation happens quite frequently in the hospital emergency room as well as in small medical centers where the scan examinations per day can be very few.

Therefore, in this case the injection system is maintained in a standby condition (represented by step 520 in FIG. 5) waiting for a new injection procedure to be started.

The method according to present disclosure evaluates, i.e. calculates, the period of time $t_{ni}$ (i.e. time to next injection) that has passed since the end (completion) of the first (i.e. previous) injection procedure, and then it compares the obtained (calculated) time value $t_{ni}$ with a predetermined de-clamping time value $t_d$ that is considered to be suitable for avoiding the stickiness problems mentioned above.

Therefore, two different situations can occur.

In the first situation, a successive (next) injection procedure is started (represented by step 540 in FIG. 5) before the predetermined de-clamping time value $t_d$ is reached (represented by step 530 in FIG. 5, where $t_{ni} \leq t_d$). Therefore, the operator carries out all the necessary steps mentioned above for properly operating the injection system and performing the scan examination of a successive patient to be treated. When also this further injection procedure is completed, the injection system is entered in a new standby condition (step 520) as previously disclosed, and the system is reiterated till the usage time of the delivery arrangement is elapsed and a new one is required to be installed.

In the second situation, a successive (next) injection procedure is not started before the predetermined de-clamping time value $t_d$ is reached (step 550 in FIG. 5, where $t_{ni} > t_d$). Therefore, according to the method of the present disclosure, the injection system 100 automatically activates the clamping means 300 associated to the delivery arrangement 135 of each supply station 105a, 105b, 105c in order to de-clamp the delivery arrangement 135 (step 560) so that it can recover its original shape for a predetermined de-clamping time duration. This means that the arrangement delivery 135, that was kept in a clamped state during the standby condition (step 520), is automatically released from its clamped (i.e. squeezed) condition and it can recover its original cylindrical shape. Once the predetermined de-clamping time duration is terminated, the injection system 100 automatically activates the clamping means 300 to clamp again the delivery arrangement 135 (step 570), and the injection system 100 starts a new standby condition (step 520). Starting a new standby condition means that the injection system automatically starts evaluating, i.e. calculating, the period of time that passes since the end of the last (i.e. previous) de-clamping step (560) (i.e. the time to next injection $t_{ni}$ is computed), and then it compares this obtained (calculated) time value $t_{ni}$ with said predetermined de-clamping time value $t_d$ as previously disclosed.

Figure 6:
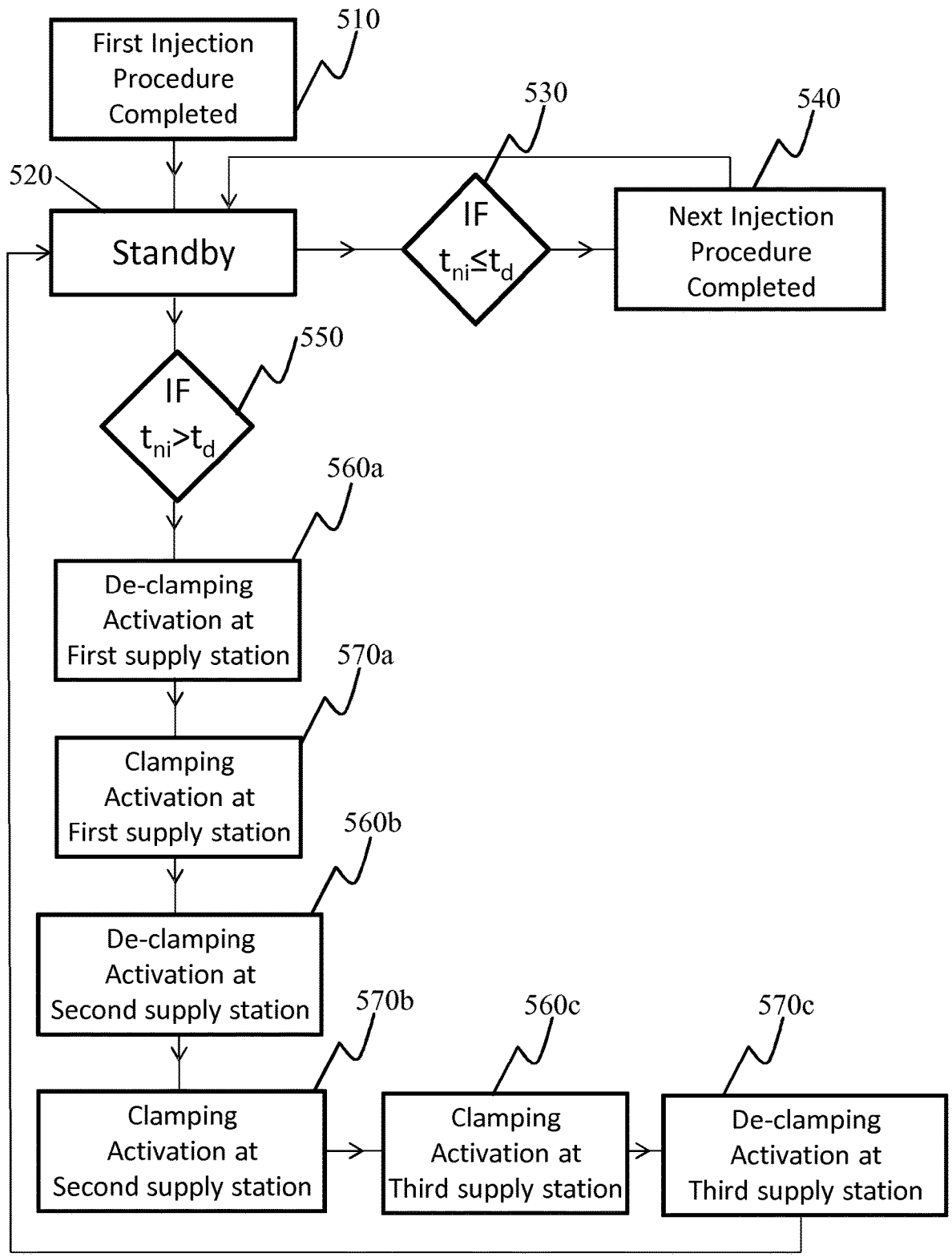
FIG. 6 shows a detailed flow chart of the method of the present disclosure with reference to the injection system of FIG. 1.

Referring now to FIG. 6, a flow chart is shown for better explaining the method of operating an injection system according to an embodiment of the present disclosure, wherein the injection system comprises three distinct supply stations 105a, 105b, 105c as shown in FIG. 1.

For sake of clarity, same reference numbers present both in FIG. 5 and FIG. 6 are used to indicate same or similar steps.

In detail, step 510 indicates that a first injection procedure on a first patient is completed and the delivery arrangement 135 is not discarded since it is still within its 24 hours usage time.

If the injection system 100 is not operated to treat a second patient immediately after the first injection procedure is completed, the injection system is maintained in a standby condition (520 of FIG. 6) waiting for a successive injection procedure to be started.

At this stage, the method according to present disclosure evaluates, i.e. calculates, the period of time $t_{ni}$ (i.e. time to next injection) that has passed since the end of the first (i.e. previous) injection procedure, and then it compares this obtained (calculated) time value with a predetermined de-clamping time value $t_d$ that is suitable for avoiding the stickiness problems mentioned above.

Therefore, two different situations can occur.

In the first situation, a successive (second) injection procedure is started (step 540 of FIG. 6) before the predetermined de-clamping time value $t_d$ is reached (step 530 of FIG. 6, according to which the condition $t_{ni} \leq t_d$ is met). Thus, the operator performs again all the necessary steps mentioned above for properly operating the injection system and executing the scan examination of the second (successive) patient. Once also the second injection procedure is completed, the injection system is maintained in a new (further) standby condition (step 520) as previously disclosed.

In the second situation, a successive (second) injection procedure is not started before the predetermined de-clamping time value $t_d$ is reached (step 550 of FIG. 6, where $t_{ni}$>$t_d$). Therefore, according to the method of the present disclosure, the injection system 100 automatically activates the clamping means 300 associated to the delivery arrangement 135 of the first supply station 105a to de-clamp the tubing 141a (step 560a) so that it can recover its original shape for a predetermined de-clamping time duration. Once the predetermined de-clamping time duration is terminated, the injection system 100 automatically activates the clamping means 300 to clamp again the tubing 141a (step 570a). After the tubing 141a has been clamped, the injection system 100 automatically activates the clamping means 300 associated to the delivery arrangement 135 of the second supply station 105b to de-clamp the tubing 141b (step 560b) so that it can recover its original shape for a predetermined de-clamping time duration. Once the predetermined de-clamping time duration is terminated the injection system 100 automatically activates the clamping means 300 to clamp again the tubing 141b (step 570b). Finally, after the tubing 141b has been clamped, the injection system 100 automatically activates the clamping means 300 associated to the delivery arrangement 135 of the third supply station 105c to de-clamp the tubing 141c (step 560c) so that it can recover its original shape for a predetermined de-clamping time duration. Once the predetermined de-clamping time duration is terminated, the injection system 100 automatically activates the clamping means 300 to clamp again the tubing 141c (step 570c) and the injection system starts a new standby condition (step 520). In the new standby condition (step 520) the injection system automatically starts again evaluating, i.e. calculating, the period of time that passes since the end of the last (i.e. previous) de-clamping step (560c) (i.e. the next time to injection $t_{ni}$ is computed by the injection system), and then it compares this obtained (calculated) time value with said predetermined de-clamping time value $t_d$ as previously disclosed.

Furthermore, in case more than one supply station is envisaged, it can be pointed out that it is not relevant the order according to which the supply lines are de-clamped (and successively clamped). In the above embodiment, de-clamping was firstly performed on the tubing associated to the first supply station, then on the tubing associated to the second supply station, and finally on the tubing associated to the third supply station. However, there's no need to follow the above order and any desired order can be followed without impairing the final outcome of the injection procedure.

Moreover, after de-clamping of one supply line (tubing) has been executed, the Applicant noticed that there's no need to immediately proceed to the de-clamping of the successive supply line. This means that there could be a pause time between successive de-clamping steps since this pause time does not negatively affect the injection procedure. However, it is preferable to execute all the required de-clamping steps in a limited period of time in order to complete this procedural step, and thus preferably the de-clamping steps are carried out substantially in a consecutive manner.

Therefore, according to an embodiment, the present disclosure relates to a method of operating an injection system comprising a pressurizing unit and at least one supply station for supplying a medical fluid to the pressurizing unit, said supply station comprising:
  at least one receptacle for containing said medical fluid;
  a delivery arrangement in fluid communication with the receptacle and the pressurizing unit for delivering the medical fluid to a patient, and
  clamping means associated with the delivery arrangement for regulating the flow of the medical fluid through the delivery arrangement,
said method comprising the steps of:
  operating the pressurizing unit till a first injection procedure is completed;
  maintaining the injection system in a standby condition before a successive (next) injection procedure is started, the injection system being not operated to inject during said step of maintaining, and
  operating the pressurizing unit till the successive (next) injection procedure is completed,
characterized in that the step of maintaining the injection system in a standby condition comprises the step of acting on said clamping means for de-clamping the delivery arrangement.

According to an embodiment of the present disclosure, the step of acting on said clamping means for de-clamping the delivery arrangement is actuated at a predetermined de-clamping frequency.

According to an embodiment of the present disclosure, the step of maintaining the injection system in a standby condition comprises the step of preserving, during the successive (next) injection procedure, the delivery arrangement used during a previous (i.e. first) injection procedure.

According to an embodiment of the present disclosure, the step of acting on said clamping means for de-clamping the delivery arrangement is actuated if a starting time of the successive injection procedure is greater than a predetermined de-clamping time.

In case the step of acting on said clamping means for de-clamping the delivery arrangement is actuated for the first time, the starting time of the successive (i.e. second) injection procedure is calculated from the completion of the first injection procedure.

On the contrary, in case at least one step of acting on said clamping means for de-clamping the delivery arrangement has already been actuated during the same step of maintaining, the starting time of the successive injection procedure is reset and calculated (computed) from the completion of the latest of the at least one step of acting on said clamping means. In other words, it may happen that the injection system is maintained in a standby condition for a long period of time and, thus, that more than one step of acting on said clamping means for de-clamping the delivery arrangement is actuated during this long period of time. Therefore, in this case the starting time of the successive injection procedure is calculated (computed) starting from the end of the last step of acting on the clamping means.

According to an embodiment of the present disclosure, the predetermined de-clamping time is selected in the range from 1 hr to 4 hr. Preferably, the predetermined de-clamping time is selected in the range from 2 hr to 3 hr.

As mentioned above, the step of acting on the clamping means for de-clamping the delivery arrangement is carried out for a predetermined de-clamping time duration. Preferably, the predetermined de-clamping time duration is selected in the range from 1 s to 2 s. More preferably, the predetermined de-clamping time duration is 1 s.

According to an embodiment, the step of maintaining the injection system in a standby condition comprises the step of acting on the clamping means for clamping the delivery arrangement. Preferably, the step of acting on the clamping means for clamping the delivery arrangement is carried out after the step of acting on the clamping means for de-clamping the delivery arrangement. More preferably, the step of acting on the clamping means for clamping the delivery arrangement is carried out immediately after the step of acting on the clamping means for de-clamping the delivery arrangement According to an embodiment, the step of maintaining the injection system in a standby condition comprises the step of calculating (computing) the starting time of the successive injection procedure. Particularly, the step of maintaining the injection system in a standby condition comprises the step of comparing the predetermined de-clamping time with the starting time of the successive injection procedure obtained from the step of computing.

According to the present disclosure, the step of acting on said clamping means for de-clamping the delivery arrangement is carried out automatically. Analogously, the step of acting on said clamping means for clamping the delivery arrangement is carried out automatically.

As mentioned above, in case the injection system comprises a first supply station and a second supply station, the step of maintaining the injection system in a standby condition comprises the step of activating the clamping means associated to the first supply station for de-clamping the tubing of the respective delivery arrangement according to the predetermined de-clamping frequency and for a predetermined de-clamping time duration, and the step of successively activating the clamping means associated to the first supply station. Moreover, the step of maintaining the injection system in a standby condition comprises the step of activating the clamping means associated to the second supply station for de-clamping the tubing of the respective delivery arrangement according to the predetermined de-clamping frequency and for a predetermined de-clamping time duration, said step of activating the clamping means associated to the second supply station being carried out after the step of activating the clamping means associated to the first supply station, and the step of successively activating the clamping means associated to the second supply station. Moreover, the step of maintaining the injection system in a standby condition comprises the step of activating the clamping means associated to the third supply station for de-clamping the tubing of the respective delivery arrangement according to the predetermined de-clamping frequency and for a predetermined de-clamping time duration, the step of activating the clamping means associated to the third supply station being carried out after the step of activating the clamping means associated to the second supply station, and the step of successively activating the clamping means associated to the third supply station.

The tubing of the delivery arrangement is made from a plastic material. Preferably the tubing of the delivery arrangement is made from silicone.

According to an embodiment, the present disclosure relates to a method of operating an injection system comprising at least one supply station for supplying a medical fluid to be injected into a patient's vasculature, said supply station comprising:

at least one receptacle for containing said medical fluid;

a delivery arrangement in fluid communication with the receptacle for delivering the medical fluid to a patient, and clamping means associated with the delivery arrangement for regulating the flow of the medical fluid through the delivery arrangement, said method comprising the steps of:

injecting the medical fluid into the vasculature of a first patient till an injection procedure expected for this first patient is completed;

maintaining the injection system in a standby condition before injecting the medical fluid into the vasculature of a second patient, and injecting the medical fluid into the vasculature of the second patient till an injection procedure expected for the second patient is completed, characterized in that the step of maintaining the injection system in a standby condition comprises the step of acting on said clamping means for de-clamping the delivery arrangement.

Experimental Data

The Applicant performed several tests in order to define the appropriate values of de-clamping frequency (i.e. de-clamping time), and time opening (i.e. de-clamping time duration) of an injector's clamping means.

Two CT Exprès injectors (manufactured by Bracco Injeneering S.A.)—in the following referenced as Injector A and Injector B—were installed for carrying out the tests. The injectors were equipped with two contrast medium supply stations and one saline supply station as shown in FIG. 1. In detail, two bottles of 500 ml of Ultravist 300 and one saline bag of 500 ml were installed. The new delivery arrangement was provided suitable for being kept installed for a period of time of 24 hours. The tubings (141a, 141b, 141c) of the delivery arrangement were made from silicone. The two injectors included the software modification according to the method of operating the injection system of the present disclosure (i.e. using a delivery arrangement having a usage time of 24 hours).

As a first step (for both the injectors) an automatic priming step was performed with the contrast agent in order to verify that the delivery arrangement did not contain air bubbles. Then three injections of contrast agent (each followed by a post-flush injection of saline) were run by using 100 mL of contrast agent and 100 mL of saline.

The following tests were carried out at different de-clamping times and at different de-clamping time durations:

TABLE 1

(Injector A)

| De-clamping Time (hr) | De-clamping Time Duration (s) | RESULT |
|---|---|---|
| 12 | 1 | negative |
| 8 | 0.5 | positive |
| 8 | 1 | negative |
| 6 | 1 | positive |
| 6 | 0.5 | positive |
| 4 | 1 | positive |
| 2 | 1 | positive |
| 1 | 1 | positive |

TABLE 2

(Injector B)

| De-clamping Time (hr) | De-clamping Time Duration (s) | RESULT |
|---|---|---|
| 12 | 1 | negative |
| 8 | 0.5 | negative |
| 8 | 1 | negative |
| 6 | 1 | negative |
| 6 | 0.5 | negative |
| 4 | 1 | positive |
| 2 | 1 | positive |
| 1 | 1 | positive |

In the "Result" column of the tables, the term "negative" means that at least one tubing of the delivery arrangement was stuck due to the prolonged action of the clamping means and the de-clamping action did not occur or it occurred only partially, while the term "positive" means that the delivery arrangement did not experience stickiness problems and the de-clamping was correctly performed.

The tests results clearly indicate that the injection system was suitably operated (with no stickiness problems) by selecting a de-clamping time comprised in the range from 1 hr to 4 hr.

The Applicant noticed that the de-clamping frequency (i.e. the de-clamping time) was the most critical factor for a successfully operating the injection system.

Therefore this specific parameter (i.e. the de-clamping frequency or the de-clamping time) was considered to be more important than the de-clamping time duration which then was selected by the Applicant as the shortest possible de-clamping time duration (in order to keep the de-clamping step to a minimum overall duration).

Modifications

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

For example, an embodiment provides an injection system. However, the injection system may be of any type (for example, with another pressurizing system like a syringe injector, with a ceiling mount for mounting it on the ceiling of an imaging suite).

In an embodiment, the injection system is for injecting one or more fluids into a patient. However, the fluids may be in any number and of any type (for example, whatever medical fluid to be used in a generic medical application for diagnostic or therapeutic purposes, such as a drug or a body fluid, or more generally to be used in any other treatment, such as for cosmetic purposes); moreover, the fluid may be injected in any way (for example, intra-arterially) into any (human or animal) patient.

In an embodiment, the injection system comprises one or more supply stations each one for supplying one of the fluids to be injected. However, the injection system may comprise any number of supply stations (down to a single one) for supplying the same or different fluids (in any combination).

In an embodiment, the injection system is for injecting the fluids into the patient during a scan examination thereof; the fluids are one or more medical fluids comprising a contrast agent and/or a saline solution. However, the injection system may be used for any scan examination (for example, in MR, nuclear or ultrasound imaging applications); moreover, the injection system may be used with any contrast agent (for example, a barium-based contrast agent such as barium sulfate, gadolinium, a radioisotope, a suspension of gas-filled microbubbles), any saline solution (for example, with the addition of dextrose), any combination thereof or more generally with any medical fluid(s).

The invention claimed is:

1. Method of operating an injection system (100; 200) comprising a pressurizing unit (140) and at least one supply station (105a; 105b; 105c) for supplying a medical fluid to the pressurizing unit, said at least one supply station comprising:
   at least one receptacle (110a; 110b; 110c) for containing said medical fluid;
   a delivery arrangement (135) in fluid communication with the receptacle and the pressurizing unit for delivering the medical fluid to a patient, and
   clamping means (300) associated with the delivery arrangement for regulating the flow of the medical fluid through the delivery arrangement,
said method comprising the steps of:
   operating (510) the pressurizing unit till a first injection procedure is completed;
   maintaining (520) the injection system in a standby condition before a successive injection procedure is started, the injection system being not operated to inject during said step of maintaining, and
   operating (540) the pressurizing unit till the successive injection procedure is completed,
characterized in that the step of maintaining the injection system in a standby condition comprises the step of acting (560) on said clamping means for de-clamping the delivery arrangement.

2. The method of operating the injection system (100; 200) according to claim 1, wherein the step of acting on said clamping means for de-clamping the delivery arrangement is performed at a predetermined de-clamping frequency.

3. The method of operating the injection system (100; 200) according to claim 1, wherein the step of acting on said clamping means for de-clamping the delivery arrangement is actuated if a starting time of the successive injection procedure ($t_{ni}$) is greater than a predetermined de-clamping time ($t_d$).

4. The method of operating the injection system (100; 200) according to claim 3, wherein the starting time of the successive injection procedure ($t_{ni}$) is calculated from the completion of the first injection procedure.

5. The method of operating the injection system (100; 200) according to claim 4, wherein the step of maintaining (520) the injection system in a standby condition comprises the step of computing the starting time of the successive injection procedure ($t_{ni}$).

6. The method of operating the injection system (100; 200) according to claim 5, wherein the step of maintaining (520) the injection system in a standby condition comprises the step of comparing the predetermined de-clamping time ($t_d$) with the starting time of the successive injection procedure ($t_{ni}$) obtained from the step of computing.

7. The method of operating the injection system (100; 200) according to claim 3, wherein, when at least one step of acting on said clamping means for de-clamping the delivery arrangement has already been actuated during the same step of maintaining, the starting time of the successive injection procedure ($t_{ni}$) is reset and calculated from the completion of the latest of the at least one step of acting on said clamping means.

8. The method of operating the injection system (100; 200) according to claim 3, wherein the predetermined de-clamping time ($t_d$) is selected in the range from 1 hr to 4 hr.

9. The method of operating the injection system (100; 200) according to claim 8, wherein the predetermined de-clamping time ($t_d$) is selected in the range from 2 hr to 3 hr.

10. The method of operating the injection system (100; 200) according to claim 1, wherein the step of acting (560) on said clamping means for de-clamping the delivery arrangement is carried out for a predetermined de-clamping time duration.

11. The method of operating the injection system (100; 200) according to claim 10, wherein the predetermined de-clamping time duration is selected in the range from 1 s to 2 s.

12. The method of operating the injection system (100; 200) according to claim 1, wherein the step of maintaining (520) the injection system in a standby condition comprises the step of acting (570) on said clamping means for clamping the delivery arrangement.

13. The method of operating the injection system (100; 200) according to claim 12, wherein the step of acting (570) on said clamping means for clamping the delivery arrangement is carried out after the step of acting (560) on said clamping means for de-clamping the delivery arrangement.

14. The method of operating the injection system (100; 200) according to claim 13, wherein the step of acting (560) on said clamping means for de-clamping the delivery arrangement and the step of acting (570) on said clamping means for clamping the delivery arrangement are carried out automatically.

15. The method of operating the injection system (100; 200) according to claim 1, wherein the at least one supply station comprises a first clamping means associated to a first supply station (105a) and a second clamping means associated to a second supply station (105b), wherein the step of maintaining the injection system in a standby condition comprises the steps of:
activating (560a) the first clamping means associated to the first supply station for de-clamping the tubing (141a) of the respective delivery arrangement according to the predetermined de-clamping frequency and for a predetermined de-clamping time duration, and
successively activating (570a) the first clamping means associated to the first supply station.

16. The method of operating the injection system (100; 200) according to claim 15, wherein the step of maintaining the injection system in a standby condition comprises the steps of:
activating (560b) the second clamping means associated to the second supply station for de-clamping the tubing (141b) of the respective delivery arrangement according to the predetermined de-clamping frequency and for a predetermined de-clamping time duration, said step of activating (560b) the second clamping means associated to the second supply station being carried out after the step of activating (570a) the first clamping means associated to the first supply station, and
successively activating (570b) the second clamping means associated to the second supply station.

17. The method of operating the injection system (100; 200) according to claim 16, wherein the injection system further comprises a third clamping means associated to a third supply station (105c), and wherein the step of maintaining the injection system in a standby condition comprises the steps of:
activating (560c) the third clamping means associated to the third supply station for de-clamping the tubing (141c) of the respective delivery arrangement according to the predetermined de-clamping frequency and for a predetermined de-clamping time duration, said step of activating (560c) the third clamping means associated to the third supply station being carried out after the step of activating (570b) the second clamping means associated to the second supply station, and
successively activating (570c) the third clamping means associated to the third supply station.

\* \* \* \* \*